(12) United States Patent
Duineveld et al.

(10) Patent No.: US 11,850,339 B2
(45) Date of Patent: Dec. 26, 2023

(54) EXPRESSION KIT FOR A BREAST PUMP DEVICE

(71) Applicant: KONINKLIJKE PHILIPS N.V., Eindhoven (NL)

(72) Inventors: Paulus Cornelis Duineveld, Drachten (NL); Johannes Petrus Antonius Maria Van Asseldonk, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 497 days.

(21) Appl. No.: 16/470,823

(22) PCT Filed: Dec. 21, 2017

(86) PCT No.: PCT/EP2017/084179
§ 371 (c)(1),
(2) Date: Jun. 18, 2019

(87) PCT Pub. No.: WO2018/115331
PCT Pub. Date: Jun. 28, 2018

(65) Prior Publication Data
US 2020/0086020 A1    Mar. 19, 2020

(30) Foreign Application Priority Data

Dec. 22, 2016 (EP) .................................... 16206123
Feb. 27, 2017 (EP) .................................... 17158164

(51) Int. Cl.
*A61M 1/06* (2006.01)

(52) U.S. Cl.
CPC .............. *A61M 1/06* (2013.01); *A61M 1/064* (2014.02); *A61M 1/0697* (2021.05); *A61M 1/06935* (2021.05); *A61M 2205/7536* (2013.01)

(58) Field of Classification Search
CPC ...... A61M 2205/11; A61M 2205/7536; A61M 1/007; A61M 2210/1007; A61M 1/06;
(Continued)

(56) References Cited

U.S. PATENT DOCUMENTS 5,071,403 A * 12/1991 Larsson .................. A61M 1/06
604/320
6,267,926 B1 * 7/2001 Reed .................. B01D 19/0031
604/4.01
(Continued)

FOREIGN PATENT DOCUMENTS

WO    2008057218 A2    5/2008
WO    2014045159 A1    3/2014
(Continued)

*Primary Examiner* — Brandy S Lee
*Assistant Examiner* — William R Frehe

(57) ABSTRACT

An expression kit (2) for use in a breast pump device (1) for extracting breast milk from a human breast comprises a breast pump body (20) having a first pressure chamber (21), a second pressure chamber (22), and a membrane portion (5) separating the first and the second pressure chamber (21, 22) from each other. The membrane portion (5) is configured to form a barrier between the first and the second pressure chamber (21, 22) for preventing leakage of human breast milk from the second pressure chamber (22) to the first pressure chamber (21), yet to allow for air exchange between the first and the second pressure chamber (21, 22), wherein the membrane portion (5) is hydrophobic and has the shape of a solid sheet being provided with holes (50) which are configured for rendering the sheet permeable to air and impermeable to liquid.

16 Claims, 3 Drawing Sheets

(58) Field of Classification Search
CPC ...... A61M 1/062; A61M 1/064; A61M 1/066; A61M 1/068; A61M 1/067; A61M 1/0697; A61M 1/069; A61M 1/06935; A61B 2018/00333; A61J 13/00
See application file for complete search history.

(56) References Cited

U.S. PATENT DOCUMENTS

| | | | |
|---|---|---|---|
| 6,581,594 B1* | 6/2003 | Drew | A61M 16/0644 |
| | | | 128/207.12 |
| 8,052,635 B1* | 11/2011 | Kelly | A61M 1/75 |
| | | | 604/74 |
| 2003/0004459 A1 | 1/2003 | McKendry | |
| 2007/0005006 A1 | 1/2007 | Rosenfeld | |
| 2012/0116299 A1 | 5/2012 | Tack | |
| 2012/0240935 A1* | 9/2012 | Johansen | A61M 16/06 |
| | | | 128/205.17 |
| 2015/0328380 A1 | 11/2015 | Furrer | |
| 2016/0015155 A1 | 1/2016 | Patel | |
| 2017/0072119 A1* | 3/2017 | Aalders | A61M 1/064 |
| 2018/0043084 A1* | 2/2018 | Keaney | A61M 1/3635 |
| 2018/0154055 A1* | 6/2018 | Alvarez | A61M 1/82 |

FOREIGN PATENT DOCUMENTS

| | | |
|---|---|---|
| WO | 2015150225 A1 | 10/2015 |
| WO | 2016145198 A1 | 9/2016 |

* cited by examiner

EXPRESSION KIT FOR A BREAST PUMP DEVICE

This application is the U.S. National Phase application under 35 U.S.C. § 371 of International Application No. PCT/EP2017/084179, filed on Dec. 21, 2017 and International Application No. 16206123.8, filed Dec. 22, 2016 and International Application No. 17158164.8 filed Feb. 27, 2017. These applications are hereby incorporated by reference herein.

FIELD OF THE INVENTION

The invention relates to an expression kit for a breast pump device for extracting breast milk from a human breast, the expression kit comprising a breast pump body having a first pressure chamber, a second pressure chamber, and a membrane portion separating the first and the second pressure chamber from each other, wherein the first pressure chamber is configured for connection to a pressure unit for generating a pressure in the first pressure chamber, wherein the second pressure chamber comprises a breast-receiving funnel, a milk outlet, and a milk path from the breast-receiving funnel to the milk outlet, and wherein the membrane portion is configured to form a barrier between the first and the second pressure chamber for preventing leakage of human breast milk from the second pressure chamber to the first pressure chamber, yet to allow for air exchange between the first and the second pressure chamber.

The invention also relates to a breast pump device for extracting breast milk from at least one human breast, the breast pump device comprising at least one expression kit as mentioned, and a pressure unit for generating a pressure in the first pressure chamber of the breast pump body of the expression kit.

BACKGROUND OF THE INVENTION

Breast pump devices are well known devices for extracting milk from a breast of a user, or two breasts simultaneously. A breast pump device may be used if the baby or infant is not itself able to extract milk from the breast, or if the mother is separated from the baby or infant, and the baby or infant is to be fed with breast milk by someone else. Hence, in general, breast pump devices are used by mothers to express breast milk at a convenient time, to be stored for later consumption by their child. A breast pump device may also be helpful in a situation in which it is desired to stimulate and increase milk production in women with a low milk supply.

A breast pump device is typically operated with one or two expression kits. Among other things, an expression kit comprises a breast-receiving funnel for receiving a user's breast, which funnel may be equipped with pads or the like for massaging the breast in a certain way, and is designed for connection to a pressure unit for realizing a pressure cycle in the breast-receiving funnel, by means of which milk expression from the breast is enabled. In practical cases, the pressure unit comprises an electric vacuum pump. The fact is that by generating a pressure cycle, particularly a vacuum cycle, possibly accompanied by a certain way of massaging the breast, a simulation of a feeding action is obtained, which triggers the necessary let-down reflex in the user of the breast pump device. For the sake of completeness, it is noted that the term "vacuum" as used in this text refers to a negative pressure with respect to ambient pressure, i.e. a pressure that is significantly lower than ambient pressure.

For hygienic reasons, most breast pump devices are equipped with a diaphragm which is configured and arranged such as to act as a shield between the breast and the pressure unit. In particular, such a diaphragm is a non-permeable resilient silicone diaphragm, which needs to make a stroke for the purpose of creating a vacuum at the breast. A pressure unit in the form of a vacuum pump is operated to cause the diaphragm to flex, thereby expanding the air in the breast-receiving funnel and creating the required vacuum at the breast as a result thereof. When the vacuum at the pump side is released, the diaphragm will move back to its rest position. As the vacuum at the vacuum pump is indirectly causing the vacuum at the breast, the hygienic function of the diaphragm is implemented. This concept is well-established and has been used in the field of breast pump devices for many years.

US 2012/116299 A1 discloses a breast pump device in which a deformation of a non-permeable resilient silicone membrane as the diaphragm creates a negative pressure in the breast-receiving funnel.

WO 2014/045159 A1 discloses another breast pump device with a non-permeable deformable membrane as the diaphragm. The breast pump device comprises a limiter to limit a deformation of the membrane. A stroke volume of the membrane can thus be limited.

WO 2008/057218 A2 discloses another breast pump device with a non-permeable resilient diaphragm as a barrier which prevents contamination from entering a vacuum pump air line.

U.S. Pat. No. 5,071,403 relates to protecting the vacuum pump of a breast pump assembly from fouling by breast milk. Air being drawn toward the vacuum pump passes through a porous body disposed in an air passage interconnecting the vacuum pump and a breast-contacting hood. When milk reaches the porous body and wets it, air may no longer pass through the porous body at least where the porous body is wet. Depending upon the extent of contact of milk with the porous body, the amount of vacuum that reaches an interior of the breast-contacting hood is reduced or eliminated, so that further expression of milk is reduced or eliminated. In the process, the continued flow of air to the vacuum pump is reduced or halted in order to protect the pump. Hence, the hydrophilic porous body serves as a barrier across a vacuum line which protects the pump.

US 2003/004459 A1 discloses a breast pump device with an optional hydrophilic filter for added isolation of the vacuum pump and vacuum lines.

WO 2015/150225 A1 discloses an expression kit for a breast pump device. The expression kit comprises a breast pump body having a first pressure chamber and a second pressure chamber, wherein the first pressure chamber is configured for connection to a pressure unit for generating a pressure in the first pressure chamber, and wherein the second pressure chamber comprises a breast-receiving funnel, a milk outlet, and a milk path from the breast-receiving funnel to the milk outlet. The first and the second pressure chamber are separated by a breathable membrane, which is gas-permeable and liquid-impermeable, for separating the first pressure chamber from liquid in the milk path, wherein the breathable membrane is a hydrophobic membrane.

Besides having a movable membrane or a porous membrane, it is possible to have a labyrinth in a breast pump device for avoiding a situation in which breast milk can be exchanged between a breast-receiving side and a pump side. The various known options involve disadvantages. The movable membrane is an expensive additional component which requires cleaning. Also, the housing for such a membrane has a non-appealing appearance, and hampers nipple visibility and cleanability, while the movement of the membrane during operation costs energy. The porous membrane is difficult to mount in the intended position and hard to keep clean, and is known for breaking easily. A labyrinth is not 100% safe and cannot be considered as being foolproof.

SUMMARY OF THE INVENTION

It is an object of the invention to provide an expression kit which is improved with respect to what is known in the art, at least as far as the realization of the diaphragm which is applied as a shield between the breast-receiving side of the expression kit and the side of the expression kit for connection to a pressure unit is concerned.

According to the invention, an expression kit is provided, which comprises a breast pump body having a first pressure chamber, a second pressure chamber, and a membrane portion separating the first and the second pressure chamber from each other, as mentioned in the opening paragraph, wherein the membrane portion is hydrophobic and has the shape of a solid sheet being provided with holes which are configured for rendering the sheet permeable to air and impermeable to liquid.

It follows from the foregoing definition that the expression kit according to the invention is equipped with a membrane portion which is another type of diaphragm than any of the known types of diaphragms as mentioned earlier. In particular, the membrane portion, which is present at the interface of the first and the second pressure chamber, is hydrophobic and has the shape of a solid sheet being provided with holes which are configured for rendering the sheet permeable to air and impermeable to liquid, particularly human breast milk and/or water. A solid sheet should be understood such as to be a sheet having a continuous appearance. Only at the position of the holes, the sheet is interrupted for the purpose of allowing air to flow through the sheet. During the manufacturing process of the membrane portion, the holes can be made in any suitable way. In general, the holes can be made by material removing techniques, which is typically done when a solid basic sheet is made first, or the holes can be made by material blocking techniques, which is typically done when the holes are made in a sheet which is formed in some kind of molding process.

It follows from the foregoing that the design of the membrane portion is relatively simple. It may be so that there is nothing more to it than the solid sheet which is provided with the holes. This allows for a design in which the membrane portion is a plastic piece, for example, wherein there is no need for an application of complex filter materials, and wherein there is no need for a design with several layers. What's more, this allows for a design in which the membrane portion is arranged in the breast pump body as an integral part thereof. For example, the membrane portion may be located in the breast pump body as a wall portion of the breast pump body. Such a design is very advantageous in that a robust expression kit having a minimum number of components can be realized. In particular, it may be so that the membrane portion and a portion of the breast pump body directly surrounding the membrane portion constitute one single, continuous piece. In that case, there is one single, continuous piece having an area provided with holes that is intended to serve as the membrane portion. On the other hand, it is possible for the membrane portion to be welded to surrounding material of the breast pump body, in which case the membrane portion is initially provided as a separate part. In general, it is possible for the membrane portion to be fixedly connected to surrounding material of the breast pump body. The membrane portion may have a planar appearance, or may be curved, whatever is appropriate in a certain design of the breast pump body.

Having a membrane portion with hydrophobic properties involves the advantage that the membrane portion repels breast milk and water. Hence, droplets of breast milk and/or water can clear off the membrane portion automatically. This ensures that a sufficient area of the membrane portion is available for air exchange between the first and the second pressure chamber under all circumstances.

In the context of the invention, it is possible to have a design of the expression kit in which the entire breast pump body is made of one single material, which may be an appropriate plastic material. Thus, the invention does not only allow for a design involving a minimum number of components, but also for a design involving a minimum number of materials. Especially in case the membrane portion and a portion of the breast pump body directly surrounding the membrane portion constitute one single, continuous piece, the membrane portion is in fact formed by a group of holes at an appropriate position in the breast pump body. In comparison to known constructions in which the membrane portion is provided as a replaceable insertion element, such a construction is very sturdy. According to the invention, the entire breast pump body can be made of a rigid plastic, wherein a portion of the breast pump body where tiny holes are present serves as the membrane portion. In such a case, the membrane portion is practically not susceptible to wear and does not need replacement during the lifespan of the expression kit. Another advantage resides in the fact that a cleaning action can be performed without needing to take special care of the membrane portion. The membrane portion and, if so desired, other portions of the breast pump body can easily be cleaned by means of a brush or in a dishwasher, which is not possible in conventional situations.

As mentioned in the foregoing, the holes of the membrane portion can be made by material removing techniques. For example, the holes may be cut holes. In particular, the holes may be laser cut holes. Applying laser techniques during the manufacturing process of the membrane portion allows for providing the holes with diameters in the micrometer range at a sufficiently high accuracy. According to another option, the holes may be drilled holes. Alternatively, it is possible for the membrane portion to be a molding product.

The membrane portion serves for allowing air to pass and constituting a barrier to liquid. In order to realize this functionality of the membrane portion in an actual embodiment of the expression kit, the size of the holes of the membrane portion may be chosen such that a diameter of the holes is in a range of 1-100 μm, and preferably in a range of 5-60 μm, wherein it is noted that the holes may have a substantially circular periphery, although this is not necessary. Furthermore, the hydrophobic features of a material of the membrane portion may be chosen such that a surface tension of the material is in a range of 0.015 N/m to 0.035 N/m. Due to the small size of the holes and the high surface tension of the material, it is not possible for human breast milk and water to block the holes, and it is not possible for such liquids to pass through the membrane portion either. No breast milk or other contamination will stick to the membrane portion, so that the membrane portion is kept clean and the holes are left open. The holes are large enough for allowing air to pass through the membrane portion under the influence of a pumping action from a pressure unit.

It is practical for the membrane portion to comprise a transparent material, because in such a case, it is possible for a user to perform a visual inspection of the membrane portion in order to see whether it needs cleaning. Contrariwise, known diaphragms are often of a multi-layer construction and comprise non-transparent materials. Materials which are suitable for use in the membrane portion include polymethylpentene (PMP) and polypropylene (PP), which are well known for their hydrophobic features. For the sake of completeness, it is noted that the membrane portion is advantageously of a single-layer construction.

In a practical embodiment of the expression kit according to the invention, the first pressure chamber is configured for receipt and airtight connection of a connector of a pressure unit. As already mentioned in respect of the prior art, the pressure unit may comprise a vacuum pump. A practical position of the first pressure chamber in the expression kit is a position in which the first pressure chamber is located at a backside of the breast-receiving funnel, i.e. on another side than the side intended for facing a user's breast.

Various advantages features of the breathable membrane of the expression kit known from WO 2015/150225 A1 are equally applicable to the hydrophobic membrane portion of the expression kit according to the invention.

In the first place, in the relatively simple construction with the solid sheet and the holes in the sheet, it is logical to assume that the membrane portion is permeable to air and impermeable to liquid in both possible directions, i.e. from the first pressure chamber to the second pressure chamber, and from the second pressure chamber to the first pressure chamber. Thus, in the construction according to the invention, the fact is that air can pass from the first pressure chamber to the second pressure chamber, and from the second pressure chamber to the first pressure chamber, whereas liquid is blocked in both directions. In contrast to a one-way permeable membrane portion, such a two-way membrane portion avoids a continuous build-up of vacuum pressure at the breast which may cause discomfort to the user.

In the second place, at least a section of the membrane portion may be arranged at an angle with respect to the milk outlet. Advantageously, a section of the membrane portion or the entire membrane portion is thereby oriented at an angle with respect to a horizontal plane when the expression kit is applied to a breast. In other words, it is advantageous for at least a section of the membrane portion to be in a non-horizontal orientation during typical use of the expression kit, because in such a case, droplets of breast milk and/or another liquid such as water can clear off the membrane portion automatically since they are drawn away by gravity.

In the third place, the expression kit may comprise a splash guard arranged between the milk path and the membrane portion, in which case the splash guard acts as an additional shield for preventing breast milk from reaching the membrane portion.

In the fourth place, the breast pump body of the expression kit may be designed such that at least one of the first pressure chamber and the second pressure chamber is configured to enable free access to the membrane portion, which is advantageous in view of cleaning purposes.

Besides the first and the second pressure chamber, and the membrane portion, the expression kit may further comprise a milk receptacle for connection to the milk outlet. The expression kit may comprise a fitting to enable a receptacle such as a milk-collection bottle having a cooperating fitting to be coupled to the breast pump body. Alternatively, the milk receptacle is part of the breast pump body. Advantageously, the design of the expression kit is such that during use, the milk flows into the receptacle under the influence of gravity.

The pressure unit can be a manual or electric pump which is arranged directly at the expression kit or at a remote location. The pressure unit is configured for connection to the first pressure chamber. A remote pressure unit can be connected to the first pressure unit by a tube system. Hence, the breast pump device can optionally comprise a tube system for connection of the expression kit to a remote pressure unit.

The present invention furthermore relates to a breast pump device for extracting breast milk from at least one human breast, the breast pump comprising at least one expression kit as described in the foregoing, particularly an expression kit comprising a breast pump body incorporating a membrane portion which is hydrophobic and has the shape of a solid sheet being provided with holes, and a pressure unit for generating a pressure in the first pressure chamber of the breast pump body.

The above-described and other aspects of the invention will be apparent from and elucidated with reference to the following detailed description of an embodiment of a breast pump device comprising an expression kit for application to a breast and a pressure unit connected to the expression kit for generating a pressure cycle by means of which milk expression from the breast is enabled.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
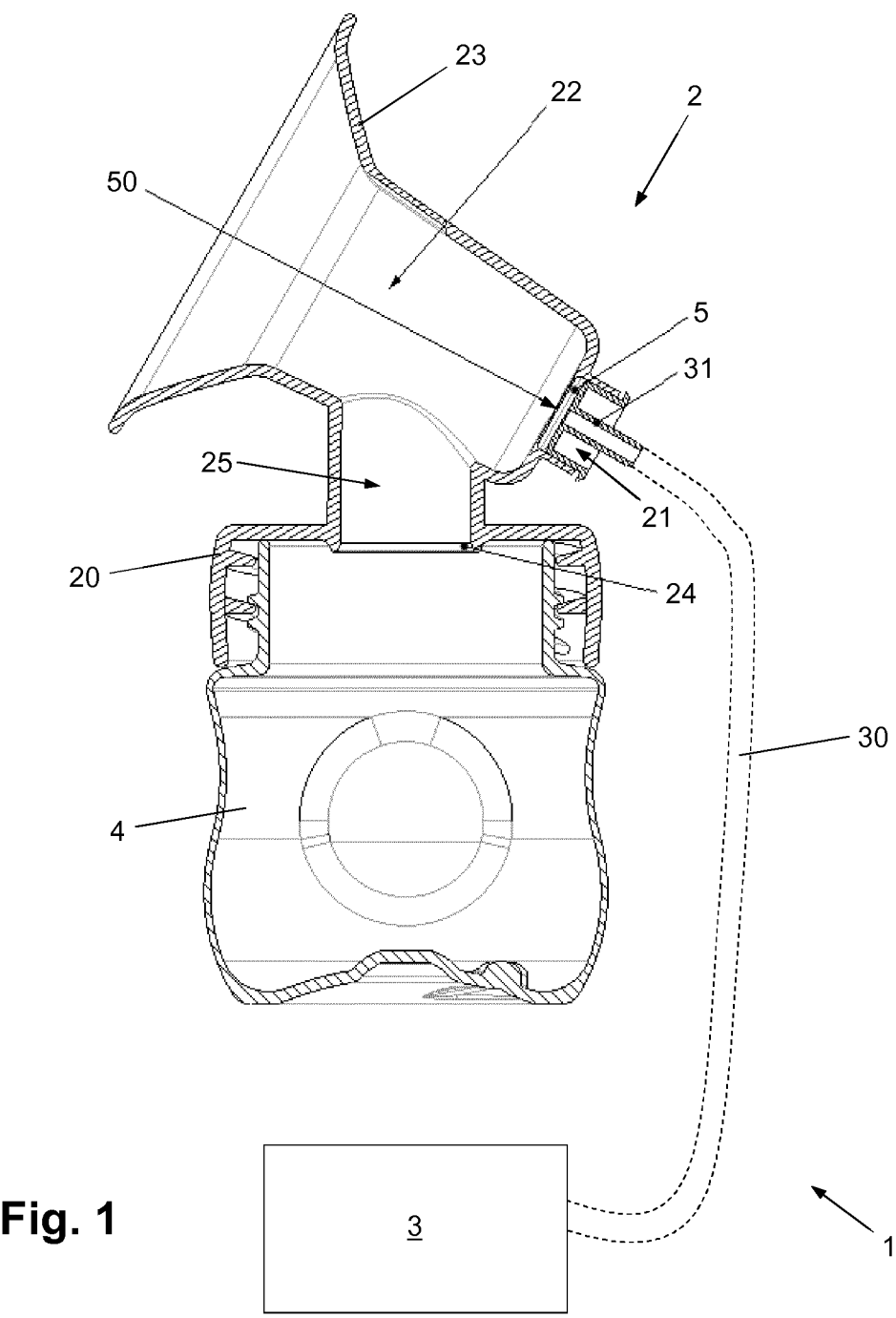
FIG. 1 diagrammatically shows a breast pump device according to the invention, comprising an expression kit and a pressure unit connected to the expression kit through a tube, wherein the expression kit and a connector of the tube are shown in a sectional view, wherein the tube is indicated with dashed lines, and wherein the pressure unit is depicted as a block.
Figure 2:
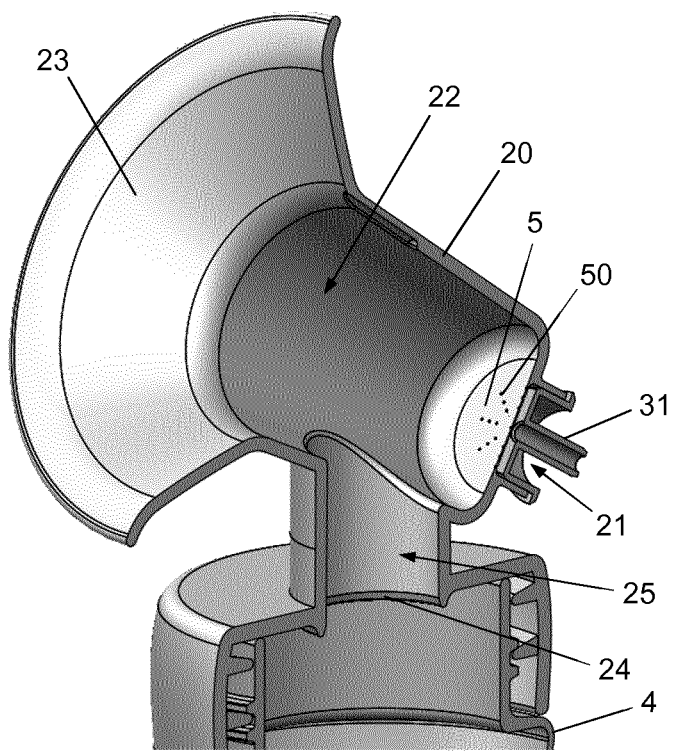
FIG. 2 diagrammatically shows a sectional perspective view of a portion of the expression kit and the connector of the tube.
Figure 3:
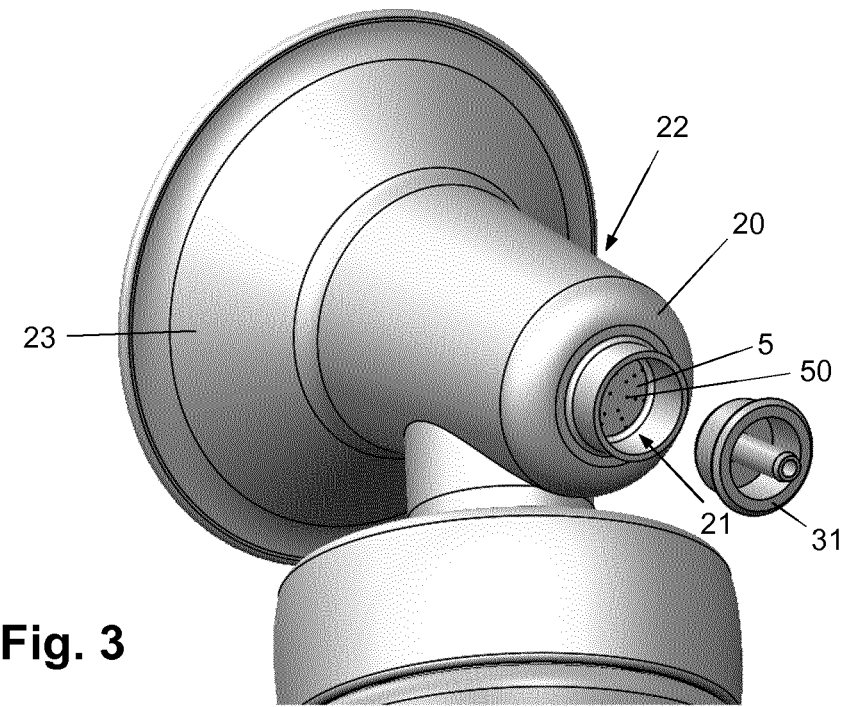
FIG. 3 diagrammatically shows a perspective view of a portion of the expression kit and the connector of the tube, wherein the connector is shown separately from the expression kit.

FIGS. 1-3 relate to a breast pump device 1 according to the invention, comprising an expression kit 2 and a pressure unit 3 for generating a pressure cycle during which vacuum is alternately created and released. The expression kit 2 comprises a breast pump body 20 and a milk receptacle 4 which is connectable to the breast pump body 20, e.g. by screwing, thereby closing a lower end of the breast pump body 20. The pressure unit 3 may comprise any suitable means for generating a pressure, and may be an electric vacuum unit, for example, or a manual pressure unit or pump. The pressure unit 3 is connected to the expression kit 2 through a tube 30. Such a configuration allows for a remote arrangement of the pressure unit 3 with respect to the expression kit 2, so that the size of that part of the breast pump device 1 which is to be applied to a user's breast can be kept within reasonable limits. That does not alter the fact that it is possible for the pressure unit 3 to be directly arranged at the expression kit 2, which may especially be useful when the pressure unit 3 is manually driven.

The breast pump body 20 of the expression kit 2 has a first pressure chamber 21 and a second pressure chamber 22. The first pressure chamber 21 is configured for receiving a connector 31 of the tube 30, the connector 31 being arranged on the tube 30 at an end of the tube 30. The tube 30 may be fixedly connected to the pressure unit 3 at the other end thereof, but it also possible for the tube 30 to be releasably connected to the pressure unit 3 through a suitable connector (not shown).

It should be noted that the breast pump device 1 can comprise two expression kits 2 for enabling a user of the breast pump device 1 to extract milk from two breasts at the same time, in which case the expression kits 2 can share a common pressure unit 3.

The second pressure chamber 22 comprises a breast-receiving funnel 23, an aperture acting as a milk outlet 24, and a milk path 25 from the breast-receiving funnel 23 to the milk outlet 24. The breast-receiving funnel 23 is thus in fluid communication with the milk outlet 24 through the milk path 25. Optionally, a one-way valve is arranged at the milk outlet 24, for letting breast milk pass from the second pressure chamber 22 to the milk receptacle 4. The breast-receiving funnel 23 can comprise a massage cushion or the like (not shown) for providing a soft and warm feel to the breast and/or imitating a baby's sucking action. In the shown example, the first pressure chamber 21 is located at a backside of the breast-receiving funnel 23. Within the framework of the invention, other locations of the first pressure chamber 21 are possible, including a location at the milk receptacle 4 in case there is no valve at the milk outlet 24.

The first pressure chamber 21 and the second pressure chamber 22 are separated at the position of a membrane portion 5, which is located in the breast pump body 20 as a wall portion of the breast pump body 20 in the shown embodiment of the expression kit 2. The membrane portion 5 is realized as a solid sheet being provided with a number of holes 50 having dimensions in the micrometer range. Furthermore, at least at the position of the membrane portion 5, the material of the breast pump body 20 has hydrophobic properties. As a result thereof, the membrane portion 5 is air-permeable and liquid-impermeable. The membrane portion 5 serves for separating the first pressure chamber 21 from the milk path 25 in the second pressure chamber 22, thereby increasing the level of hygiene of the breast pump device 1 and preventing liquid from reaching the tube 30 and possibly also the pressure unit 3, while allowing for air communication between the first pressure chamber 21 and the second pressure chamber 22, at least to such an extent that the breast milk expression functionality of the breast pump device 1 is not hampered, wherein the membrane portion 5 provides a sufficiently low pneumatic restriction to the air flow. For example, a vacuum applied to the first pressure chamber 21 also causes vacuum in the second pressure chamber 22 since air can pass through the membrane portion 5, whereas water and/or breast milk in the second pressure chamber 22 are blocked. Thereby, the membrane portion 5 acts as a hygienic shield. Being hydrophobic may further positively influence bacteria-retention at the membrane portion 5, so that bacteria transfer to the tube 30 and the pressure unit 3 are prevented.

It is possible for the breast pump body 20 to be equipped with a splash guard (not shown) arranged in the second pressure chamber 22 for shielding the membrane portion 5 from droplets of breast milk. Thereby, such a splash guard can act as a first barrier which avoids that too much breast milk reaches the membrane portion 5. Droplets of breast milk which reach the membrane portion 5 anyway can clear off the membrane portion 5 automatically due to the hydrophobic features of the membrane portion 5.

The holes 50 of the membrane portion 5 may be arranged according to any suitable pattern. The pattern as can be seen in FIGS. 2 and 3 is just one example of many possibilities. The holes 50 may be laser cut holes, which does not alter the fact that during the manufacturing process of the breast pump body 20, other techniques than laser techniques may be put to practice for the purpose of creating the holes 50. The area of the membrane portion 5 can have a substantially circular periphery, as can be seen best in FIGS. 2 and 3.

Advantageously, the entire breast pump body 20 is made of one single material, preferably a clear plastic material having hydrophobic properties, such as polymethylpentene (PMP) or polypropylene (PP). It is possible for the membrane portion 5 to be provided as an element that is fixedly connected to the surrounding portion of the breast pump body 20, but it is preferred to have a membrane portion 5 which constitutes one single, continuous piece with the directly surrounding portion of the breast pump body 20. In other words, it is preferred if the breast pump body 20 is made as an integral entirety, wherein the membrane portion 5 is not an inserted element or the like, but is simply defined as a wall portion of the breast pump body 20 where a group of holes 50 is present. In such a case, the expression kit 2 is very much user-friendly, as the user does not need to bother about the membrane portion 5 in any way. Contrary to what is known in the art, the membrane portion 5 does not constitute a portion of the breast pump body 20 that is more susceptible to damage than the remainder of the breast pump body 20, which facilitates both use and cleaning of the expression kit 2.

General operational aspects of the breast pump device 1 will now be mentioned. In the first place, a user makes sure that the expression kit 2 and the pressure unit 3 are properly connected to each other through the tube 30 and the connector 31. Before the pressure unit 3 is activated, the user furthermore needs to take care that the milk receptacle 4 is properly connected to the breast pump body 20, and that the breast to be subjected to a milk extraction process is properly inserted into the breast-receiving funnel 23 of the second pressure chamber 22. In that situation, a breast-receiving end of the second pressure chamber 22 is sealingly closed by the breast, whereas a lower end of the second pressure chamber 22 is sealingly closed by the milk receptacle 4. When, starting from that situation, the pressure unit 3 is activated, a pressure cycle involving generation and release of vacuum is realized in the first pressure chamber 21, as a result of which the breast is subjected to forces which serve for simulating a feeding situation, as a result of which milk supply is induced from the breast, and during which it happens that air is sucked in the first pressure chamber 21 from the second pressure chamber 22 through the holes 50 of the membrane portion 5. A desired pressure profile, i.e. a time-variable pressure, can be applied to the breast taking into account the pneumatic restriction of the membrane portion 5. The breast milk flows from the breast-receiving funnel 23 to the milk receptacle 4 through the milk path 25 and the milk outlet 24, under the influence of gravity and/or the pressure generated by the pressure unit 3.

Figure 4:
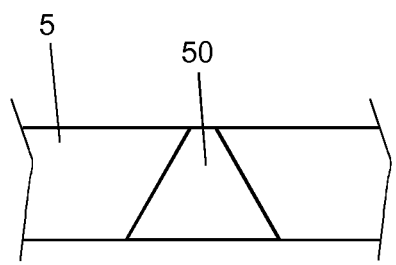
FIGS. 4 and 5 illustrate two practical shapes of holes as arranged in a membrane portion that is part of the expression kit, showing a sectional view of a portion of a membrane portion in which a hole is present.
Figure 5:
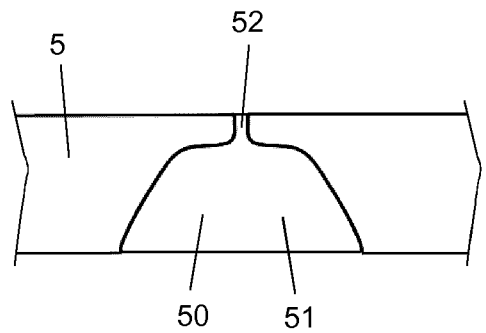

The holes 50 of the membrane portion 5 can be of any suitable design, being through holes which are capable of allowing air to pass from one side of the membrane portion 5 to the other. The holes 50 may have a substantially circular periphery, which does not alter the fact that other peripheral shapes are possible as well. FIGS. 4 and 5 serve to illustrate the fact that it is preferred for the holes 50 to have a generally tapered shape, at least along a part of the length thereof. In FIG. 4, an example of a hole 50 which is tapered along the entire length thereof is shown, whereas in FIG. 5, an example of a hole 50 which is partially tapered is shown, the latter hole 50 including a relatively wide tapering portion 51 and a relatively small non-tapering portion 52.

The fact is that by having holes 50 which are at least partially tapered, pressure losses over the membrane portion 5 are significantly reduced and it is more difficult for liquid to enter the hole. Reducing the number of holes 50 involves facilitating the manufacturing process. An at least partially tapered design of the holes 50 can easily be realized in an injection molding process or a combination of injection molding and laser cutting, for example. The number of holes 50 as compared to a situation in which a diameter of the holes 50 is substantially constant along the length of the holes 50 can be at least 50% less, and it may even be so that the number is reduced with a factor of 10, without a significant increase of the overall size of the membrane portion 5. It may also be so that the thickness of the membrane portion 5 can be reduced. Hence, by having the at least partially tapered design of the holes 50, it is possible to manufacture the membrane portion 5 as a mass product by using standard mass manufacturing techniques such as molding. In this respect, it is noted that the manufacturing process of the hole 50 as shown in FIG. 5 may involve the steps of making a large hole 51 that does not go completely through the material of the membrane portion 5 with a first laser shot, and making a smaller hole 52 with a second laser shot for opening the remaining material of the membrane portion 5 at the bottom of the large hole 51 so as to have a through hole 50 as a result. Alternatively, the hole 50 as shown can also be made through injection molding, possibly combined with laser techniques. In any case, it is also possible for the smaller hole 52 to be provided with a tapered shape.

It follows from the foregoing that the invention provides a breast pump device 1 and an expression kit 2 for use in the breast pump device 1. The invention is particularly related to the membrane portion 5, which is present at the interface of the first pressure chamber 21 and the second pressure chamber 22 of the breast pump body 20 of the expression kit 2, and which serves as a hygienic shield between the first pressure chamber 21 and the second pressure chamber 22, i.e. between a location of the breast pump device 1 for receiving a user's breast and the pressure unit 3 which is used for generating the pressure which is required for enabling the breast milk expression functionality of the breast pump device 1. According to the invention, the membrane portion 5 has hydrophobic features and has the shape of a solid sheet being provided with holes 50 which are configured for rendering the sheet permeable to air and impermeable to liquid. It is preferred for the membrane portion 5 to be arranged in the breast pump body 20 as an integral part thereof, wherein the membrane portion 5 may be arranged in the breast pump body 20 as a wall portion of the breast pump body 20, in which case it is possible that the breast pump body 20 is an integral entirety in which the membrane portion 5 is defined by an area where the holes 50 are present. Hence, within the framework of the invention, it is possible to have a membrane portion 5 which is in fact nothing more than holes in a rigid plastic portion, which is a very sturdy membrane portion 5 that is hardly susceptible to wear and that can easily be cleaned.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

For the sake of clarity, it is noted that the term "holes" as used in this text for indicating that the membrane portion 5 is provided with holes 50 is to be understood as to implicitly refer to through holes, i.e. holes which go all the way through the membrane portion 5, from one side of the membrane portion 5 to the other.

The invention claimed is:

1. An expression kit for a breast pump device configured for extracting breast milk from a human breast, the expression kit comprising a breast pump body having a first pressure chamber, a second pressure chamber, and a breast pump membrane portion separating the first pressure chamber from the second pressure chamber, wherein the breast pump membrane portion is of continuous construction with the breast pump body, and wherein
the first pressure chamber is configured for connection to a pressure unit for generating a pressure in the first pressure chamber,
the second pressure chamber comprises a breast-receiving funnel, a milk outlet, and a milk path from the breast-receiving funnel to the milk outlet,
the breast pump membrane portion is defined as a rigid backside wall of the breast pump body opposite the breast-receiving funnel, such that the breast pump membrane portion separates the first pressure chamber from the milk path in the second pressure chamber and is configured for preventing leakage of the breast milk from the second pressure chamber to the first pressure chamber, yet to allow for air exchange between the first pressure chamber and the second pressure chamber, and the breast pump membrane portion is hydrophobic and has the shape of a solid sheet of continuous construction and being provided with cut holes configured for rendering the solid sheet permeable to air and impermeable to liquid, wherein the breast pump membrane portion is a single layer.

2. The expression kit according to claim 1, wherein the breast pump membrane portion is arranged in the breast pump body as an integral part thereof.

3. The expression kit according to claim 1, wherein an entirety of the breast pump body is made of one single plastic material.

4. The expression kit according to claim 1, wherein the cut holes of the breast pump membrane portion are laser cut holes.

5. The expression kit according to claim 1, wherein the cut holes of the breast pump membrane portion have a diameter in a range of 5-60 μm.

6. The expression kit according to claim 1, wherein the cut holes are tapered along at least a portion of a length thereof.

7. The expression kit according to claim 1, wherein the breast pump membrane portion comprises a material having a surface tension in a range of 0.015 N/m to 0.035 N/m.

8. The expression kit according to claim 1, wherein the breast pump membrane portion comprises a transparent material.

9. The expression kit according to claim 1, wherein the breast pump membrane portion comprises polymethylpentene (PMP).

10. The expression kit according to claim 1, wherein the first pressure chamber is configured for receipt and airtight accommodation of a connector of the pressure unit.

11. A breast pump device configured for extracting breast milk from at least one human breast, the breast pump device comprising at least one expression kit according to claim 1, and
the pressure unit for generating the pressure in the first pressure chamber of the breast pump body of the expression kit.

12. The expression kit according to claim 1, wherein the cut holes of the breast pump membrane portion have a diameter in a range of 1-100 μm.

13. The expression kit according to claim 1, wherein the breast pump membrane portion has a circular periphery.

14. The expression kit according to claim 1, wherein the cut holes are partially tapered.

15. The expression kit according to claim 1, further comprising a milk receptacle for connection to the milk outlet.

16. The expression kit according to claim 1, wherein a milk receptacle is part of the breast pump body.

* * * * *